(12) United States Patent
Siurkus et al.

(10) Patent No.: US 11,364,273 B2
(45) Date of Patent: Jun. 21, 2022

(54) **TOPICAL COMPOSITION WITH ACTIVE COMPOUNDS FROM *CANNABIS SATIVA* AND *CALENDULA OFFICINALIS* FOR REDUCTION OF SKIN LESIONS**

(71) Applicant: UAB SATIMED, Utena (LT)

(72) Inventors: Juozas Siurkus, Kaisiadorys (LT); Rimantas Peciura, Kaunas (LT)

(73) Assignee: UAB STAIMED, Utena (LT)

( * ) Notice: Subject to any disclaimer, the term of this patent is extended or adjusted under 35 U.S.C. 154(b) by 673 days.

(21) Appl. No.: 16/091,049

(22) PCT Filed: Apr. 4, 2017

(86) PCT No.: PCT/IB2017/051911
§ 371 (c)(1),
(2) Date: Oct. 3, 2018

(87) PCT Pub. No.: WO2017/175126
PCT Pub. Date: Oct. 12, 2017

(65) Prior Publication Data
US 2019/0111093 A1 Apr. 18, 2019

(30) Foreign Application Priority Data

Apr. 4, 2016 (LT) ...................... 2016 044

(51) Int. Cl.
| | | |
|---|---|---|
| *A61K 36/28* | (2006.01) | |
| *A61K 36/886* | (2006.01) | |
| *A61K 36/63* | (2006.01) | |
| *A61K 36/185* | (2006.01) | |
| *A61K 8/41* | (2006.01) | |
| *A61K 8/97* | (2017.01) | |
| *A61K 8/36* | (2006.01) | |
| *A61K 8/34* | (2006.01) | |
| *A61K 8/81* | (2006.01) | |
| *A61K 9/06* | (2006.01) | |
| *A61Q 19/00* | (2006.01) | |
| *A61K 8/37* | (2006.01) | |
| *A61K 8/67* | (2006.01) | |
| *A61K 8/92* | (2006.01) | |
| *A61Q 17/04* | (2006.01) | |
| *A61K 8/9789* | (2017.01) | |

(Continued)

(52) U.S. Cl.
CPC ............... *A61K 36/28* (2013.01); *A61K 8/34* (2013.01); *A61K 8/345* (2013.01); *A61K 8/361* (2013.01); *A61K 8/375* (2013.01); *A61K 8/41* (2013.01); *A61K 8/678* (2013.01); *A61K 8/8152* (2013.01); *A61K 8/922* (2013.01); *A61K 8/97* (2013.01); *A61K 8/9789* (2017.08); *A61K 9/0014* (2013.01); *A61K 9/06* (2013.01); *A61K 31/192* (2013.01); *A61K 36/185* (2013.01); *A61K 36/63* (2013.01); *A61K 36/886* (2013.01); *A61K 47/10* (2013.01); *A61K 47/14* (2013.01); *A61K 47/18* (2013.01); *A61K 47/22* (2013.01); *A61K 47/32* (2013.01); *A61K 47/44* (2013.01); *A61P 17/02* (2018.01); *A61P 17/06* (2018.01); *A61Q 17/04* (2013.01); *A61Q 19/00* (2013.01); *A61Q 19/005* (2013.01); *A61Q 19/007* (2013.01); *A61K 2236/37* (2013.01)

(58) Field of Classification Search
CPC .. A61K 2300/00; A61K 36/185; A61K 36/28; A61K 36/63; A61K 36/886; A61K 2236/37; A61K 31/192; A61K 47/10; A61K 47/14; A61K 47/18; A61K 47/22; A61K 47/32; A61K 47/44; A61K 8/34; A61K 8/345; A61K 8/361; A61K 8/375; A61K 8/41; A61K 8/678; A61K 8/8152; A61K 8/922; A61K 8/97; A61K 8/9789; A61K 9/0014; A61K 9/06; A61P 17/02; A61P 17/06; A61Q 17/04; A61Q 19/00; A61Q 19/005; A61Q 19/007
See application file for complete search history.

(56) References Cited

U.S. PATENT DOCUMENTS

| | | |
|---|---|---|
| 6,949,582 B1 | 9/2005 | Wallace |
| 8,337,908 B2 | 12/2012 | Letzel et al. |

(Continued)

FOREIGN PATENT DOCUMENTS

| | | | |
|---|---|---|---|
| EP | 2 444 081 B1 | 4/2015 | |
| EP | 2444081 B1 * | 4/2015 | ............. A61K 31/19 |
| GB | 2 485 483 A | 5/2012 | |
| WO | 2009/039843 A2 | 4/2009 | |

OTHER PUBLICATIONS

Fogh et al., "Eicosanoids in skin of patients with atopic dermatitis: Prostaglandin E2 and leukotriene B4 are present in biologically active concentrations", Journal of Allergy and Clinical Immunology, 1989, pp. 450-455, vol. 83, No. 2, Part 1.

(Continued)

*Primary Examiner* — Aaron J Kosar
(74) *Attorney, Agent, or Firm* — Nixon & Vanderhye

(57) ABSTRACT

Disclosed is a topical composition including essential combination of synergistically acting phyto-active materials, non-psychotropic phytocannabinoids from the plant of *Cannabis sativa*: Cannabidiol, Cannabidiolic acid, Cannabivarin Cannabigerol in combination with extract of *Calendula* flower and the formulation of the base to ensure the features of anti-inflammation, anti-oxidation, emollient, and bactericidal components. The topical composition is an emollient dedicated for reduction of skin lesions caused by atopic dermatitis, urticaria, radiotherapy and UV induced skin damage and acne. In addition the topical composition could reduce secretion of fats, facilitate deep skin hydration, reduce pores and exert soothing effect.

4 Claims, 2 Drawing Sheets

(51) Int. Cl.
 A61P 17/06 (2006.01)
 A61P 17/02 (2006.01)
 A61K 9/00 (2006.01)
 A61K 31/192 (2006.01)
 A61K 47/10 (2017.01)
 A61K 47/14 (2017.01)
 A61K 47/18 (2017.01)
 A61K 47/22 (2006.01)
 A61K 47/32 (2006.01)
 A61K 47/44 (2017.01)

(56) References Cited

U.S. PATENT DOCUMENTS

2012/0264818 A1 10/2012 Newland
2013/0012575 A1 1/2013 Letzel et al.
2014/0302086 A1 10/2014 Kelly
2015/0044315 A1 2/2015 Letzel et al.
2018/0125905 A1 5/2018 Letzel et al.

OTHER PUBLICATIONS

Thomsen, "Atopic dermatitis: Natural history, diagnosis, and treatment", ISRN Allergy, 2014, Article ID 354250, vol. 2014.
Vasilopoulos et al., "Genetic association between an AACC insertion in the 3'UTR of the stratum corneum chymotryptic enzyme gene and atopic dermatitis", The Journal of Investigative Dermatology, 2004, pp. 62-66, vol. 123, Issue 1.
Grether-Beck et al., "Urea uptake enhances barrier function and antimicrobial defense in humans by regulating epidermal gene expression", Journal of Investigative Dermatology, 2012, pp. 1561-1572, vol. 132, No. 6.
Imokawa et al., "Decreased level of ceramides in stratum corneum of atopic dermatitis: An etiologic factor in atopic dry skin?", The Journal of Investigative Dermatology, 1991, pp. 523-526, vol. 96, No. 4.
Chiba et al., "Transmembrane proteins of tight junctions", Biochimica Et Biophysica Acta (BBA)-Biomembranes, 2008, pp. 588-600, vol. 1778, No. 3.
Brandt et al., "Th2 cytokines and atopic dermatitis", Journal of Clinical & Cellular Immunology, 2011, vol. 2, No. 3.
Biedermann et al., "Regulation of T cell immunity in atopic dermatitis by microbes: The yin and yang of cutaneous inflammation", Frontiers in Immunology, 2015, vol. 6, Article 353.
Benenson et al., "Atopic dermatitis—a risk factor for invasive *Staphylococcus aureus* infections: Two cases and review", The American Journal of Medicine, 2005, pp. 1048-1051, vol. 118, No. 9.
Moody et al., "Retapamulin: What is the role of this topical antimicrobial in the treatment of bacterial infections in atopic dermatitis?", Skin Therapy Letter, 2010, pp. 1-4, vol. 15, No. 1.
Searing et al., "Vitamin D in atopic dermatitis, asthma and allergic diseases", Immunology and Allergy Clinics North America, 2010, pp. 397-409, vol. 30, No. 3.
Kim et al., "Consensus guidelines for the treatment of atopic dermatitis in korea (part II): Systemic treatment", Annals of Dermatology, 2015, pp. 578-592, vol. 27, No. 5.
Del Rosso et al., "The clinical relevance of maintaining the functional integrity of the stratum corneum in both healthy and disease-affected skin", The Journal of Clinical and Aesthetic Dermatology, 2011, pp. 22-42, vol. 4, No. 9.
Smith et al., "Proteoglycans in Normal and Healing Skin", Advances in Wound Care (New Rochelle), 2015, pp. 152-173, vol. 4, No. 3.
Ghatak et al., "Roles of Proteoglycans and Glycosaminoglycans in Wound Healing and Fibrosis", International Journal of Cell Biology, 2015, Article 834893.
Fišar et al., "Phytocannabinoids and endocannabinoids", Current Drug Abuse Reviews, 2009, pp. 51-75, vol. 2, No. 1.
Pertwee, "The diverse CB1 and CB2 receptor pharmacology of three plant cannabinoids: Delta9-tetrahydrocannabinol, cannabidiol and delta9-tetrahydrocannabivarin", British Journal of Pharmacology, 2008, pp. 199-215, vol. 153, No. 2.
Hassan et al., "Cannabidiol enhances microglial phagocytosis via transient receptor potential (TRP) channel activation", British Journal Pharmacology, 2014, pp. 2426-2439, vol. 171, No. 9.
Ryan et al., "Cannabidiol targets mitochondria to regulate intracellular ca2+ levels", The Journal Neuroscience, 2009, pp. 2053-2063, vol. 29, No. 7.
Takeda et al., "Cannabidiolic acid as a selective cyclooxygenase-2 inhibitory component in cannabis", Drug Metabolism and Disposition, 2008, pp. 1917-1921, vol. 36, No. 9.
Ramer et al., "COX-2 and ppar-γ confer cannabidiol-induced apoptosis of human lung cancer cells", Molecular Cancer Therapeutics, 2013, pp. 69-82, vol. 12, No. 1.
Hampson et al., "Cannabidiol and (-)delta9-tetrahydrocannabinol are neuroprotective antioxidants" Proceedings of the National Academy of Sciences of the United States of America, 1998, pp. 8268-8273, vol. 95, No. 14.
MacCarrone et al., "The endocannabinoid system, anandamide and the regulation of mammalian cell apoptosis", Cell Death & Differentiation, 2003, pp. 946-955, vol. 10, No. 9.
Wilkinson et al., "Cannabinoids inhibit human keratinocyte proliferation through a non-cb1/CB2 mechanism and have a potential therapeutic value in the treatment of psoriasis", Journal of Dermatological Science, 2007, pp. 87-92, vol. 45, No. 2.
Nagarkatti et al., "Cannabinoids as novel anti-inflammatory drugs", Future Medicinal Chemistry, 2009, pp. 1333-1349. vol. 1, No. 7.
Pommier et al., "Phase III randomized trial of calendula officinalis compared with trolamine for the prevention of acute dermatitis during irradiation for breast cancer", Journal of Clinical Oncology, 2004, pp. 1447-1453, vol. 22, No. 8.
Babaee et al., "Antioxidant capacity of calendula officinalis flowers extract and prevention of radiation induced oropharyngeal mucositis in patients with head and neck cancers: A randomized controlled clinical study", Daru Journal of Pharmaceutical Sciences, 2013, vol. 21, No. 1, Article 18.
International Search Report and Written Opinion, dated Jul. 25, 2017, from corresponding PCT application No. PCT/IB2017/051911.
Izzo et al. "Non-psychotropic plant cannabinoids: New therapeutic opportunities from an ancient herb." Trends in Pharmacological Sciences; 2009. TIPS-730, (10): 515-27. Naples, Italy.
Van Der Stelt, Mario and Vincenzo Di Marzo. "Anandamide as an intracellular messenger regulating ion channel activity."; Prostaglandins & Other Lipid Mediators; vol. 77 (2005) (1-4): 111-22. Pozzuoli (NA), Italy.
Trouba et al. "Oxidative stress and its role in skin disease." Antioxidants and Redox Signaling vol. 4 No. 4: pp. 665-673. (2002) Research Triangle Park, NC.

\* cited by examiner

Data presented as group averages ± SN. Differences between control/edema and phytocannabinoid preparation groups are considered significant at $p<0.05$*.

Data presented as group averages ± SN. Differences between control/edema and phytocannabinoid preparation groups are considered significant at $p<0.05$*.

TOPICAL COMPOSITION WITH ACTIVE COMPOUNDS FROM *CANNABIS SATIVA* AND *CALENDULA OFFICINALIS* FOR REDUCTION OF SKIN LESIONS

FIELD OF THE INVENTION

Present invention relates to a topical composition comprising phytocannabinoids from the plant *Cannabis sativa* in combination with extract from *Calendula officinalis* for reduction of skin lesions caused by atopic dermatitis, urticaria, radiotherapy and UV induced skin burn damage, and acne.

BACKGROUND OF THE INVENTION

Inflammation is a biological process during which arachidonic acid is released from the phospholipid-based cell membranes and metabolized by cyclooxygenases (COX1 and COX 2) to produce regulatory molecules eicosanoids: prostaglandins or thromboxanes. The second possibility for metabolism of the arachidonic acid is the pathway controlled by lipoxygenase (LOX) where the enzymatic reaction leads to production of regulatory molecules belonging to the family of the leukotrienes. Prostaglandins play a key role in the generation of the inflammatory response. Biosynthesis of prostaglandins is significantly increased in inflamed tissue and is contributing to the development of the cardinal signs of acute inflammation. Certain eicosanoids which are derived from arachidonic acid are potent mediators of skin inflammation and modulators of certain T-lymphocyte activities (Samuelsson 1990). The levels of the cyclooxygenase product, prostaglandin E2 (PGE2) and the lipoxygenase products, leukotriene B4 (LTB4), 12- and 15-hydroxyeicosatetraenoic acid, elevated in biopsy specimens obtained by keratome from lesional, perilesional, and patients with AD and psoriasis compared to clinically unaffected patients (Fogh, Herlin and Kragballe 1989).

Atopic dermatitis (AD) is a common, clinically defined, chronic inflammatory skin disease frequently associated with allergic rhinitis, asthma and immunoglobulin E (IgE)-mediated food reactions. The high variability of the clinical phenotype and severity, genetic background and known pathomechanisms strongly suggest a high degree of pathophysiological heterogeneity. The clinical pattern of eczematous skin lesions is relatively uniform and results from interactive alterations of the skin barrier and the innate and adaptive immune systems. The pathogenesis of atopic dermatitis involves both epidermal barrier and immunologic dysfunction. A number of these alterations are caused by mutations in the genes encoding immune and barrier function proteins, which may alter the regulation or the structure of the gene product itself. Other alterations may be consequences of environmental factors such as stress, scratching behaviour, allergen exposure or washing habits (Thomsen 2014). The epidermal barrier consists of a thin layer of vital keratinocytes, which slowly differentiate into flat corneocytes while moving upwards in the epidermis. The thin layer of dead keratinocytes that make up the stratum corneum covers the vital parts of the epidermis and protects it against water loss and microbe invasion. The complex process of epidermal differentiation is disturbed in AD lesions. The corneocytes are attached to one another by corneodesmosomes which can be degraded by stratum corneum chymotryptic enzyme (SCCE). The decreased activity of SCCE inhibitor lymphoepithelial Kazal-type-related inhibitor (LEKTI) in AD skin results in increased activity of SCCE thus, the quantity of corneodesmosomes, less cohesion of cells and more shedding of the uppermost corneocytes (Vasilopoulos et al. 2004). The reduction of corneodesmosomes results in the trans-epidermal water loss and lower hydration of the stratum corneum. The consequences of complete lack of the protease inhibitor LEKTI is demonstrated by the clinical phenotype of Comel-Netherton syndrome: maximal skin barrier dysfunction and AD-like skin inflammation. Naturally the stratum corneum is slightly acidic due to the natural moisturizing factor (NMF), which consists of the filaggrin degradation products, lactic acid and urocanic acid (UCA). The optimal pH for SCCE activity is in the alkaline range, therefore, in case of LEKTI deficiency for AD patients it is highly recommended to use personal hygiene compositions with slightly acidic or neutral pH (Hovnanian 2013). Another reason of epidermal barrier loss is related to activity of profilaggrin gene (FLG), where many genetic studies of FLG have confirmed an association between this gene mutation and ichthyosis vulgaris, and clinical AD manifestations. In addition down regulated production of filaggrin at the protein level and infiltrate of T-helper type 2 (Th2) cytokines contributes to AD development in patients with no filaggrin mutations (van Smeden and Bouwstra 2016). Small molecules: urea and glycerol improve the skin barrier function. In addition the petrolatum-comprising stabilizing creams have water-sealing effect and reduce trans-epidermal water loss (Grether-Beck et al. 2012; Fluhr, Darlenski and Surber 2008). The ceramides—another group of waxy lipid molecules are an essential component to the lipid double layer of the stratum corneum, which content in the stratum corneum correlates with tran-sepidermal water loss. Therefore, strategy of supplementation of ceramides could be used for treatment of AD (Imokawa et al. 1991). Defects in tight junction formation are a factor which contributes to the barrier defects in AD. Occludin and tricellulin are transmembrane molecules which form a tight junction functioning as gates for the passage of water, ions and solutes through the paracellular pathway (Chiba et al. 2008). One of the AD cause reasons can be related with Th2-dominated immune responses and reflected by predominance of the Th2 associated cytokines and interleukins IL-4, IL-5, and IL-13. The approaches of AD treatment by modulation of immune response are targeted towards IL-4 receptor alpha chain or the cytokine thymic stromal lymphopoietin (TSLP) using specific antibodies. The epidermal dendritic cells which are hyper expressing the high-affinity IgE-receptor FceRI are common in patients with extrinsic AD. Patients with intrinsic AD lack detectable IgEs against common aero- and food allergens. Finally, targeting histamine receptors (HRs) with their antagonists is a widely used approach to treat AD, as histamine is released in response to various skin allergens and, thus, triggers a variety of effects in the skin's immune system (Brandt and Sivaprasad 2011). Infection with *Staphylococcus aureus* is very common among patients with AD as they have an imbalance in innate and acquired immunity connected to staphylococci and loss of microbiome diversity in the skin. *S. aureus* may produce exotoxins with superantigenic properties. The cell wall components, such as lipoteichoic acid and peptidoglycan of *S. aureus* are recognized by TLRs, especially TLR-2. In response to *S. aureus* produced extracellular, protein-containing vesicles, the TLR-2 polymorphism-possessing monocytes are producing AD-inflammation inducing IL-6 and IL-12, dermal fibroblasts produce cytokine TSLP (Biedermann et al. 2015; Benenson et al. 2005). The treatment of *S. aureus* colonisation is usually based either on oral or topical antibiotics which might be ineffective due to *S.*

*aureus* resistance or cause allergies, respectively (Moody, Morrison and Tyring 2010). Eczema herpeticatum (EH) is clinically defined as the disseminated infection of eczematous skin disease with the herpes simplex virus (HSV). The pathogenesis of EH is manifested by unmasking of the HSV entry receptor nectin-1, lack of plasmacytoid dendritic cells in AD lesions or cathelicidin production in situ, and an abnormal IFN-c response to HSV (Blanter et al. 2015). Vitamin D is essential for stimulation of adaptive immunity via toll-like receptors (TLRs), which increases production of pro-inflammatory cytokine, enhance of Th2 responses and enhances expression of the antimicrobial peptide LL-37 in keratinocytes. LL-37 deficiency plays a significant role in the pathogenesis of eczema herpeticum (EH). Therefore vitamin D is acting in suppression of inflammatory responses, enhancing antimicrobial peptide activity and promoting the integrity of the skin barrier permeability, and supplementation, i.e. provides a therapeutic intervention for a variety of skin disorders, including AD (Searing and Leung 2010). Some findings revealed that impaired homeostasis of oxygen/nitrogen radicals and increased oxidative stress are involved in the pathophysiology of childhood AD, and indicate that suppression of oxidative stress might be a potentially useful strategy for the treatment of AD (Omata et al. 2001). The cutaneous inflammation of AD is controlled using topical corticosteroids (TCSs) and topical calcineurin inhibitors (TCIs). The reduction of inflammation is the key for AD control. The symptoms of visible lesions on the skin appear as a secondary effect or the consequence of inflammation. The treatment of AD is based on two approaches—reactive treatment which is based on utilisation of topical corticosteroids (TCSs) and topical calcineurin inhibitors (TCIs), which exhibit different mechanisms of action on the skin barrier function and inflammatory cell infiltrate (Kim et al. 2015). The proactive AD therapy is based on application of anti-inflammatory therapy to previously affected skin, together with ongoing, long-term emollient treatment of unaffected skin. This approach targets invisible inflammation in the usually relapsing 'problem zones' of patients with AD (Del Rosso and Levin 2011).

Oxidation and skin inflammation. Many endogenous and environmental pro-oxidant agents lead to the harmful generation of reactive oxygen species (ROS) in the skin. The resulted oxidative stress damages proteins, lipids, and DNA. An imbalance between ROS and antioxidants can lead to an elevated oxidative stress level. Some evidence indicates that allergic and inflammatory skin diseases like atopic dermatitis, urticaria and psoriasis are mediated by oxidative stress (Trouba et al. 2002). For example, monocytes from patients with atopic dermatitis are primed to generate ROS in response to zymosan which is a Toll-like receptor 2 (TLR2) ligand, suggesting that *S. aureus* may damage disease lesioned skin by producing ROS. Mast cells generate, mainly, intracellular ROS following the aggregation of FcεRI; these ROS may act as secondary messengers in the induction of several other biological responses (Okayama 2005).

The radiation therapy leads to skin damage which manifests in many forms ranging from acute radiodermatitis to chronic skin fibrosis. Acute radiodermatitis is a generalized erythema that becomes visible within 90 days of radiation therapy, often between 2 and 4 weeks presenting as a blanchable sustained erythema. The majority of patients are suffering from complications of secondary radiation therapy. The severity of radiotherapy induced dermatitis is graded from 1 to 4, where grade 1 presents as a faint erythema that may demonstrate dry desquamation, epilation, or decreased sweating. Grade 2 presents as a brighter or tender erythema that demonstrates moist desquamation within skin folds and also moderate edema. This level of damage typically occurs after 4 to 5 weeks from radiotherapy when greater than 40 Gy is given. One to two weeks following the cessation of radiotherapy, this dermatitis begins to subside with an increased expression of epidermal growth factor receptors (McQuestion 2006).

The formation of bullae and the damage to the barrier function of the skin make patients more susceptible to infections, especially by *S. aureus*. Infection is, however, a rare consequence of radiodermatitis. Grade 3 involves moist desquamation outside of skin folds with pitting edema. Grade 4 is characterized by ulcerated tissue with necrosis or bleeding. When any of these acute reactions fail to resolve, progression to chronic radiodermatitis or skin fibrosis can occur (Hill et al. 2004).

Dermal hydration, which is responsible for the skin's tonicity and turgor, is maintained due to the hydrophila of proteoglycans and glycosaminoglycans such as (GAGs) that are able to retain moisture or prevent Transepidermal Water Loss (TEWL). Proteoglycans have a distinct spatial localization in normal skin and are essential for the correct structural development, organization, hydration, and functional properties of this tissue. The extracellular matrix (ECM) is no longer considered to be just an inert supportive material but is a source of directive, spatial and temporal, contextual information to the cells via components such as the proteoglycans. The impact of changes in proteoglycans on skin pathology and the wound healing process is recognized as an important area of pathobiology and is an area of intense investigation. Recent knowledge on skin proteoglycans can be used to incorporate these molecules into useful adjunct therapies for wound healing and for maintenance of optimal tissue homeostasis in aging skin. In tissues such as the skin, the repair of the dermis after wounding requires the overlying epithelial layer (keratinocytes), which together orchestrate the cytokine-mediated signalling and paracrine interactions that are required to regulate the proper extent and timing of the repair process (Smith, Melrose 2015). The importance of extracellular molecules in the microenvironment, primarily the proteoglycans and glycosaminoglycans in wound healing, cytokine cross-talk between cell types and the role of proteoglycans in regulating these processes has been recently emphasized (Ghatak et al 2015).

Pharmacological features of cannabinoids. Centuries ago the extracts of *Cannabis sativa* plant were used as pain relievers and anti-inflammatory agents. Currently, the topic of pharmacology features of cannabinoids became a great research focus and it is rapidly growing. The increasing research focus on the naturally occurring therapeutic value possessing phyto-compounds such as cannabinoids could be explained by the fact that many of the synthetic medical drugs lack therapeutic efficiency or/and may induce drastic side effects. The *C. sativa* contains 3 major classes of bioactive molecules: flavonoids, terpenoids and phytocannabinoids. The family of phytocannabinoids compromises approximately 60 types of terpenophenolic compounds, which are the most important chemicals in the *C. sativa* plant, possessing highest therapeutic value. Phytocannabinoids are the only natural analogues of the mammal endocannabinoids. Phytocannabinoids are accumulated in the glandular structures of *cannabis* plants, known as trichomes. Depending on the species, *cannabis* can accumulate 49-tetrahydrocannabinol (Δ9-THC) which is a major psychoactive ingredient and/or cannabidiols (CBD) which are non-psychoactive ingredients of *cannabis* plant (Fisar 2009). The most common, therapeutic value possessing, but non-psychoactive cannabinoids from *C. sativa* are Cannabidiol (CBD), Cannabionic acid (CBDA), Cannabichromene (CBC), Cannabicyclol (CBL), Cannabivarin (CBV), Cannabigerol (CBG), Tetrahydrocannabivarin (THCV), Cannabichromevarin (CBCV), Cannabigerovarin (CBGV), and Cannabigerol Monoethyl Ether (Fisar 2009). Family of non-psychoactive phytocannabinoids has a very low affinity towards CB1 and CB2—endocannabinoid system related receptors (Pertwee 2008). However, they modulate pharmacological effects by utilizing other endocannabinoid system related receptors, i.e. transient receptor potential (TRP) channels (Hassan et al. 2014), the peroxisome proliferators—activated receptor g (PPARg), GPR55, the putative abnormal-CBD receptor, 5-hydroxytryptamine receptor subtype 1A (5-HT1A), glycine a1 and a1b receptors, the adenosine membrane transporter phospholipase A2, lipoxygenase (LOX) and cyclooxygenase-2 (COX-2) enzymes (Izzo et al. 2009) and $Ca^{2+}$ homeostasis regulation system (Ryan et al. 2009). For example, the phytocannabinoid based anti-inflammatory action occurs via inhibition of inflammatory COX-2 protein (Takeda et al. 2008), or inhibition of inactivation of endogenous cannabinoid anandamide, which is an intracellular messenger for regulation of ion channel activity (van der Stelt and Di Marzo 2005). In addition, CBD driven modulation of intracellular $Ca^{2+}$ concentration is related to many therapeutic effects. For example, one of them is anticancer effect via generation of reactive oxygen species (ROS) for induction of apoptosis in cancer cells (Ramer et al. 2013). Cannabidiol and—Δ-9-tetrahydrocannabinol are neuroprotective antioxidants (Hampson et al. 1998). Within the human body the CB1 and CB2 receptors are interacting with the endogenous ligands—endocannabinoids, which should not be confused with their analogues—phytocannabinoids. The physiological action of endocannabinoids and psychoactive phytocannabinoids is driven via their interactions with the specific class of Gαi protein-coupled receptors known as a Central Cannabinoid Receptor (CB 1) and Peripheral Cannabinoid Receptor (CB2), respectively. The highest abundance of CB1 is located in the central nervous system (basal ganglia, hippocampus, cerebellum and cortex), where they mediate cannabinoid related psychoactive effects. In addition, the CB1 receptors are present in the nerve-terminals of testis, uterus, vascular endothelium, eye, spleen, ileum, and in adipocytes. In addition, the CB2 receptors are distributed within the immune system of the body, in the enriched areas of B lymphocytes (Schwitzer et al. 2015). The molecules of endocannabinoids are interacting with CB1 and CB2 receptors via moieties of esters, ethers, long-chain polyunsaturated fatty acids and amides. The function of endocannabinoids is mainly related with regulation of various neurotransmitter release in the peripheral and neural tissues, regulation of fat and energy metabolism and they are also very important in inflammation processes. Therefore, the components of endocannabinoid system—CB1 and CB2 receptors and endogenous cannabinoids—are the targets for the treatment of neurodegenerative (Parkinson's, Alzheimer's and Huntington's) diseases, inflammatory pain, multiple sclerosis, glaucoma, neuropathic pain, obesity and oncological diseases (Maccarrone and Finazzi-Agro 2003).

Psoriasis is an inflammatory disease characterized by epidermal keratinocyte hyper-proliferation. The most significant mediators involved in this disorder are those associated with a dominant Th1 cytokine profile. D9-THC, CBN and CBD were shown to inhibit keratinocyte proliferation in the low micromolar range and in a cannabinoid receptor-independent manner. Although the mechanism is incompletely understood, these results support a therapeutic potential of non-psychotropic cannabinoids for the treatment of psoriasis (Wilkinson and Williamson 2007; Nagarkatti et al. 2009).

*Calendula officinalis*, commonly known as Marigold, is used in the Western and Asian countries for its anti-inflammatory properties. The main active components of *calendula* are sesquiterpene and flavonol glycosides, triterpenoid saponins, triterpene alcohols, flavonoids, carotenoids, xanthophylls, phenolic acids, sterols, mucilage, tocopherols, calendulin, and bitters. According to some reports, the extract of this plant possesses some pharmacological activities which include antioxidant action, anti-inflammatory, antibacterial, antifungal, and antiviral properties. Results of one clinical trial showed that *Calendula officinalis* was highly effective in the prevention of acute dermatitis in patients with cancer undergoing postoperative irradiation (Pommier et al. 2004). It was observed that this plant has cytotoxic effect on tumour cell lines in vitro and anticancer activity in vivo. Some reports showed that mouthwash as gel formulation comprising *calendula* extract reduced radiation-induced oropharyngeal mucositis (Omata et al. 2001) in patients with head-and-neck cancer (Babaee et al. 2013). There are several examples of topical compositions comprising cannabidiol in combination with herbal extracts that can be dissolved in lipotropic solvent selected from a group consisting of triglycerides, hydrocarbons, alcohols, ketones, esters or ethers or they can be dissolved in the oil from *Cannabis sativa* seeds or they can be dissolved in hydrophilic solvent selected from the group consisting of aliphatic polar alcohols or their mixtures with water. Document EP2444081B1 2015 April 8 A composition for the treatment of inflammatory diseases comprising *Boswellia serrata* extract (15.00 (%, w/w) and *Cannabis sativa* extract 0.55 (%, w/w)) in combination with Petrolatum 38.00 (%, w/w), Ethyl oleate 20.00 (%, (w/w)), Isopropyl stearate 15.00 (%, w/w), Lanolin hydrogenated 6.00 (%, w/w), Cetyl and stearyl alcohol 4.45 (%, (w/w)), Benzyl alcohol 0.80 (%, (w/w)), Dehydroacetic acid 0.20 (%, (w/w)). Dedicated for strong and long lasting anti-inflammatory deep reaching effect, e.g. for the treatment of arthritis, muscle inflammations, eczema and psoriasis. The preparation soothes dermatitis, seborrhoea, and acne.

Another document, U.S. Pat. No. 6,949,582B1, describes the Method of relieving analgesia and reducing inflammation based on composition containing from about 97.5% to about 99.5% by weight a 70% monohydric alcohol solution, and from about 0.5% to about 2.5% by weight of a synergistic cannabinoid mixture extracted from the female plant *Cannabis sativa* L, including in combination: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), terpenoids, and flavonoids. The liniment is applied topically, preferably by spraying, and the constituents of the mixture are absorbed through the skin and interact with cannabinoid receptors in the body and tissues of a human patient to produce therapeutic analgesic and anti-inflammatory effects without undesirable psychotropic side effects.

Document US20120264818A1—Topical Compositions with *Cannabis* Extracts invention discloses a method for making a topical composition for the treatment of pain. The topical composition includes a heat-treated *cannabis* material in a carrier. The carrier is typically an aprotic solvent that serves both as an extraction solvent and a skin penetrator.

The topical composition may be applied, for example, directly to the skin or through a patch, strip, bandage, or covering.

Suitable preservatives, antioxidants, and chemical stabilizers include, for example, alcohol, benzyl alcohol, butylated hydroxyanisole, butylparaben, calcium acetate, castor oil, chlorocresol, 4-chloro-m-cresol, citric acid, disodium edetate, edetate disodium, ethoxylated alcohol, ethyl alcohol, glycerin, methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, zinc stearate, and combinations thereof.

Suitable thickening, stiffening and suspending agents include, for example, aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, bentonite, and combinations thereof.

In one embodiment, the topical composition is used to treat pain, inflammation, muscle tightness, muscle spasms, skin ulcerations, and scleroderma. In one embodiment, the topical composition is used to treat joint pain, muscle pain, or arthritis.

The topical compositions, as described herein, may also include one or more optional ingredients, for example, palliative agents, skin conditioning agents, emollients, humectants, odorants, preservatives, solvents, thickening, stiffening and suspending agents, other agents, or a combination thereof. Other optional agents may be added to the composition including, for example, aloe, *arachis* oil, benzoic acid, cocoa butter, coenzyme Q10, dimethicone, *eucalyptus* oil, resorcinol, retinol, retinyl palmitate, retinyl acetate, fennel extract, whey protein, ceramide, silicone, alpha-hydroxy acids, beta-hydroxy acids, sorbitol, vitamin A, vitamin B, vitamin C, vitamin D, vitamin E.

However, compared to the other compositions herein presented, our composition exhibits very efficient emollient features without using synthetic cytotoxic surface active materials, alcohols or polymers. The combination of cannabinoids and active compounds of *Calendula* extract results in effective anti-inflammatory features that reduce lesions caused by atopic dermatitis, eczema, urticaria, psoriasis and skin damage caused by UV or/radiation.

SUMMARY OF THE INVENTION

Herein presented invention relates to topical composition comprising *Cannabis sativa* and *Calendula* sp. extracts for treatment and/or reduction or/and prevention of lesions resulted from skin inflammation, atopic dermatitis, eczema, urticaria, psoriasis and skin damage caused by UV or/radiation therapy.

The topical composition is based on *Cannabis sativa* extract in the base of Water (Aqua), Caprylic/Capric triglyceride, *Aloe barbadensis* Leaf Juice, *Olive europaea* Fruit Oil, Glycerine, Stearic acid, non-decarboxylated and decarboxylated *cannabis* resin 3% (to introduce 0.5% phytocannabinoids, where ratio of CBDA with CBD corresponds to 1:1), Phenoxyethanol, Glyceryl Stearate, Acrylates/C10-30 Alkyl Acrylate Crosspolymer, Tocopherol, Triethanolamine. The topical composition comprises essential combination of active materials: phytocannabinoids from plant of *Cannabis sativa* (Cannabidiol (CBD), Cannabidiolic acid (CBDA), Cannabivarin (CBV) Cannabigerol (CBG)), *Calendula* sp. flower extract (0.7%) and *olive* oil. Dynamic viscosity—2100-2300 mPa, pH—6. Phytocannabinoids and *Calendula* extract exert anti-inflammatory, anti-oxidative and bactericidal features. The synergetic effect of phytocannabinoids and other active compounds from *Calendula* extract results in deep hydration, reduces skin pores and exerts great soothing effect. The natural *Olive* oil moisturises skin, stipulates elasticity and synergistically with phytocannabinoids reduces effects of oxidative and inflammatory factors which might damage the skin.

DETAILED DESCRIPTION OF THE INVENTION

Materials and Methods

Preparation of *Cannabis sativa* Extract

Figure 1:
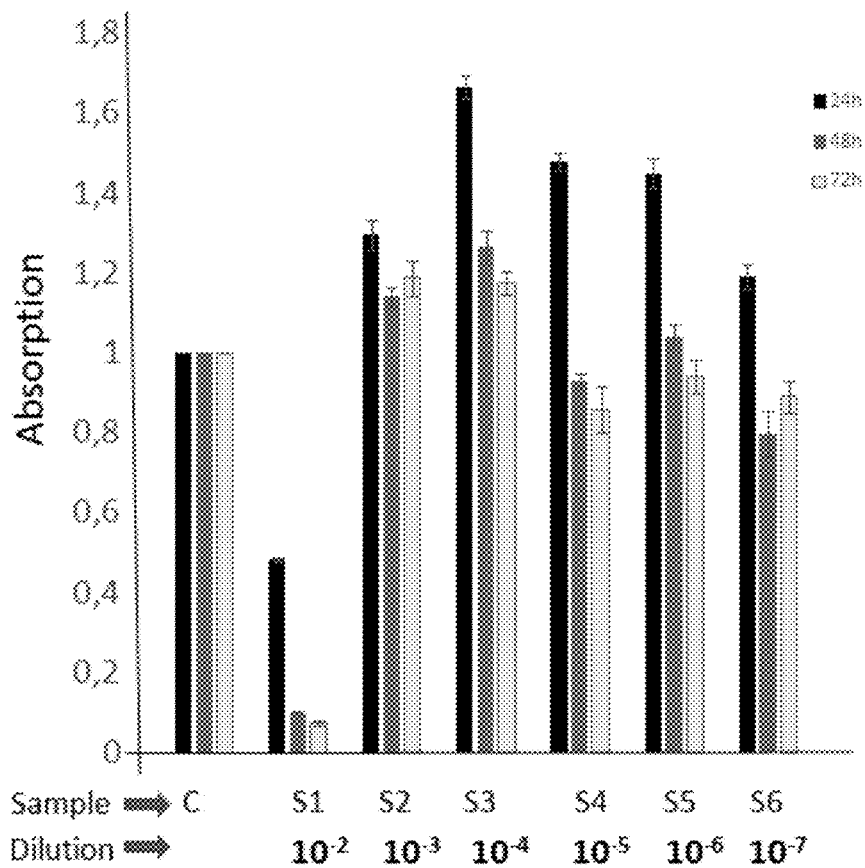
FIG. 1 shows human keratinocyte's cell viability to the exposure of diluted *Cannabis sativa* active materials after 24, 48 and 72 hours of incubation under cell optimal culturing conditions. Sample C- cell viability without exposure to any additives.

*Cannabis* extract is produced using pulverized, dried (passive drying process for 52 hours at 35-40° C., to reach residual moisture level of approximate 10%) biomass of *Cannabis sativa* "Benico" variety which is derived from the mixture comprising upper plant parts—blossoms and leaves. However, other non-psychotropic *Cannabis sativa* varieties can be used, where THC concentration rages from 0.0001 to 1%. The CBD and CBDA enriched lipophilic fraction (extract) is produced using an approach of supercritical extraction with $CO_2$ with the following parameters: pressure—465 bar, extraction temperature—70° C., process length—120 minutes. The CBD resin is produced by decarboxylation of CBDA resin at 160° C. for 5-6 hours.

The amount of major cannabinoids: CBD, CBDA, CBG, CBV, in the *cannabis* extract is determined according to the ST/NAR/40 "Recommended Methods for the Identification and Analysis of *Cannabis* Products" (United Nations, New York, 2009). 10 mg of the resin is homogenised in the 1 mL mixture of methanol and chloroform (v/v, 9:1), for 15 min in the ultrasound bath. After centrifugation for 10 min at max g to separate insolubilities, the prepared samples were analysed using Shimadzu HPLC chromatography system with 30AC automatic injector, CTO-20AC column thermostat, DGU 20A5 vacuum degas unit, LC-30AD pump and SPD-M20A diode matrix detector. The analysed cannabinoids were fractionated in Supelco Discovery HS C18

(25×4.6 mm, 5 μm; RP) with C18 pre-column under the isocratic elution conditions. The temperature of the column—30° C., mobile phase: acetonitrile 0.1%, flow 0.8 ml/min., separation time 30 min.; injection volume—20 μl; detection at the two channels 225 nm and 306 nm. The data was analysed with Lab Solutions software. The following internal standards were used from Cerilliant: Cannabinol, 1.0 mg/mL (C-046), Cannabidiolic acid (CBDA), 1.0 mg/mL (C-144), Cannabidivarin (CBDV), 1.0 mg/mL (C-140), Cannabigerol (CBG), 1.0 mg/mL (C-141).

Characteristics of *Cannabis sativa* Extract—

Protein fraction (Kjeldahl Method)—0.63%, Lipids (Soxlet Method) 96.60%, water (Gravimetric Method (103 dgr centigrade))—1.73%. Sum of CBD/CBDA/CBDV/CBG ~18%, where the extract comprises 80% of CBDA from the total cannabinoids, THC<0.1%.

Preparation of Topical Composition

| Compound | Content % | Vendor and specifications |
|---|---|---|
| Caprylic/capric triglyceride | 8.76 | |
| *Aloe barbadensis* leaf juice | 5.64 | |
| Stearic acid | 0.94 | |
| Glycerol monostearate | 0.52 | |
| Triethanolamine | 0.25 | |
| Vitamin E | 0.4 | |
| Water (Distilled) | 74.89 | |
| Olive *europaea* (Olive) Fruit Oil | 3.33 | |
| Glycerol | 3.33 | |
| Acrylates/C10-30 Alkyl Acrylate Crosspolymer (Carbopol ® Ultrez 21) | 0.6 | |
| *Calendula officinalis* Flower Extract | 0.07 | |
| Decarboxylated *Cannabis sativa* extract CBD (2.5 mg/mL) | 0.25 CBD 0.75 resin | 15-18% CBD, [Satimed] |
| Non- carboxylated *Cannabis sativa* extract CBDA (2.5 mg/mL) | 0.25 CBDA 0.75 resin | 15-18% CBDA, [Satimed] |
| Phenoxyethanol | 0.8 | |

Initially, separately the groups of the following components are mixed: (i) required amounts of Caprylic/capric triglycerides, vitamin E and *Olive europaea* (*Olive*) fruit oil, (ii) glycerol, *Aloe barbadensis* leaf juice and water, (iii) Stearic acid, Glycerol monostearate, (iv) Phenoxyethanol is dissolved in water, (v) Triethanolamine is dissolved in water (vi) and separately *Calendula officinalis* flower extract is dissolved in water followed by 2 time filtration through the filter (0.45-0.75 μm). Finally the required amount of Carbopol® Ultrez 21 is dissolved in the largest amounts of water and incubated with mixing for rehydration and soaking. The groups of components (i), (ii) and (iii) are added to reactor and incubated under the slow mixing at 65±2° C. After the temperature is equilibrated Phenoxyethanol solution is added. The homogenisation at 3000 rpm is performed for 3 minutes. After homogenisation the triethanolamine solution is added and homogenisation at 4000 rpm is repeated for 4-5 minutes. The analogical homogenisation cycles are repeated after introduction of *Calendula officinalis* Flower Extract solution and decarboxylated and non-decarboxylated extracts of *Cannabis sativa*. The homogenisation is finalized at 5000 rpm for 10 minutes at 65° C. Finally the Carbopol® Ultrez 21 solution and required amount of residual water is added. The temperature is adjusted to 70° C. and homogenisation continued at 2000 rpm for 10 minutes. The dynamic viscosity of the product was monitored using Rotational Viscometer (Fungilab, SMART Series H) and pH using Consort (C832) pH-meter. The composition is packaged into vials by maintaining the reactor temperature of 65° C. and slow stirring—60 rpm.

EXAMPLES

Example 1

Experimental Procedures

Cell Culturing.

Primary cell line of Human keratinocytes Heka (Gibco, ThermofisherScientic) was cultivated in GIBCO EpiLife serum-free cell culture medium with S7 supplement (ThermofisherScientic) in a microwell plate of 24 vials, 20,000 cells/per well, at 37° C., 5% $CO_2$. The viable cells after adhesion to the well surface were subjected to 2 μl of *Cannabis sativa* extract which is used in described topical composition. The extract was prepared after several dissolving steps in ethanol to reach dilution levels from $10^2$ to $10^7$. The blank control—raw *Cannabis sativa* seed oil was prepared analogically. The *Cannabis sativa* extract comprises 18% of cannabinoids CBD/CBDA/CBDV/CBG, and 80% of CBDA from the total cannabinoid level.

Cell Viability.

Living cells were determined using the CCK-8 kit (Cell Counting Kit, Dojingo) while following the manufacturer's instructions. The amount of formazan resulted by activity of dehydrogenases dye was measured in the diluted media spectrophotometrically at 450 nm.

Quantification of sGAG and GAG.

The evaluation of production of extracellular, membrane and intracellular glycosaminoglycans was performed using Blyscan ELISA kits for quantification of sulfonated and non-sulfonated glycosaminoglycans and hyaluronic acid using The Purple-Jelley Hyaluronan Assay (Biocolor, Life Science Assays) after 24 and 48 hours, respectively. For membrane and intracellular analysis of sGAG and GAG, normalized amounts cells were harvested and fractionated. Assays were carried out by following instructions of manufacturer using 50 and 100 μl of harvested supernatant.

Results:

*Cannabis sativa* extract from the topical composition stimulates skin hydration via stimulation of synthesis of glycosaminoglycans and proliferation of human epidermal keratinocytes in vitro.

Transepidermal water loss occurs due to water mobility and ability to move to the skin surface where it evaporates when exposed to air. sGAG production by keratinocytes maintain its content in the skin, which ensures accumulation of water and prevent dryness.

In FIG. 1, plot of absorption units reflect the response of human keratinocyte's cell viability to the exposure of diluted *Cannabis sativa* active materials after 24, 48 and 72 hours of incubation under cell optimal culturing conditions. Sample C—cell viability without exposure to any additives.

Experimental data shows that active materials of *Cannabis sativa* stimulate viability of human keratinocytes. The highest effect was observed after 24 h of cell treatment with cannabinoid entourage.

Figure 2:
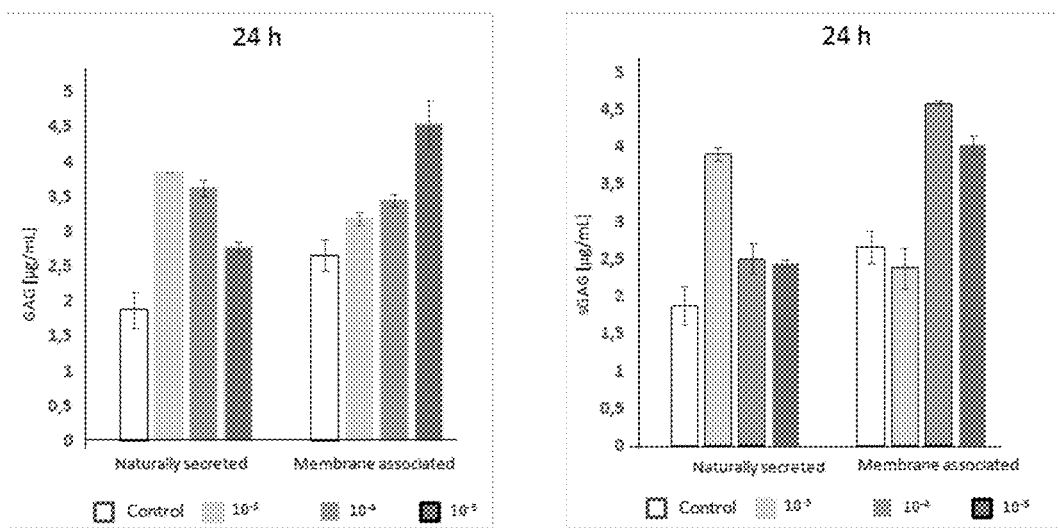
FIG. 2 shows estimated GAG and sGAG produced in response to the keratinocyte exposure to diluted active materials after 24 hours of incubation under cell optimal culturing conditions. Control corresponds to non-treated human keratinocyte culture.

In FIG. 2, the plot shows estimated GAG and sGAG produced in response to the keratinocyte exposure to diluted active materials after 24 hours of incubation under cell optimal culturing conditions. Control corresponds to non-treated human keratinocyte culture.

Experimental data shows that active materials of *Cannabis sativa* stimulate production of sGAG and GAG by human keratinocytes. The highest effect was observed after 24 h of cell treatment with the highest dilution cannabinoid entourage compared to non-treated culture. This indicates that keratinocytes exposed to the cannabinoids CBD/CBDA/CBDV/CBG increase production of GAG and sGAG molecules which are very important in protection of skin moisture balance.

Example 2

Experimental Procedures

The effects of two phytocannabinoid preparations (JSC SATIMED): "Preparation 1" (in which the concentration of phytocannabinoids is 40 mg/ml, extract diluted 4.5 fold with raw *Cannabis sativa* seed oil) and "Preparation 2" (10 mg/ml of phytocannabinoids, extract diluted 10 fold with raw *Cannabis sativa* seed oil), were analysed on the model of acute inflammation (paw edema) in mice. Three single doses of preparation "Preparation 1" (0.33 mg/kg, 1 mg/kg and 10 mg/kg phytocannabinoids) and one dose of "Preparation 2" (0.23 mg phytocannabinoids) were tested. The experiment was performed on 48 mice (BALB/c strain ♀, 6-7 weeks old, average weight 23 g), which were divided into 6 groups (6 mice per group), and in all of them paw edema was induced:

1 group. Edema/control—no treatment
2 group. 50 mg/kg prednisolone/control i.p.
3 group. 0.33 mg/kg phytocannabinoids "Preparation 1" p.o.
4 group. 1 mg/kg phytocannabinoids "Preparation 1" p.o.
5 group. 10 mg/kg phytocannabinoids "Preparation 1" p.o.
6 group. 0.23 mg phytocannabinoids "Preparation 2" (topical application) (i.p.—intraperitoneally, p.o.—orally)

Prior to the study, the thickness of the right hind foot of each mouse was measured by a digital micrometre (Mitutoyo, Japan). Acute inflammation (paw edema) was induced to all mice by an injection of 20 µl of 1% λ—carrageenan into their right paw. The effects of phytocannabinoids on acute inflammation (paw edema) were measured by analysing the differences between the thickness of the affected and unaffected paw. The test and control materials were administered to animals one hour after carrageenan injection. Digital micrometre measurements were carried out after 4, 6 and 24 hours of carrageenan injection.

Results:

*Cannabis sativa* extract of topical composition reduces inflammation of Paw edema in mice model after oral administration and topical treatment.

Figure 3:
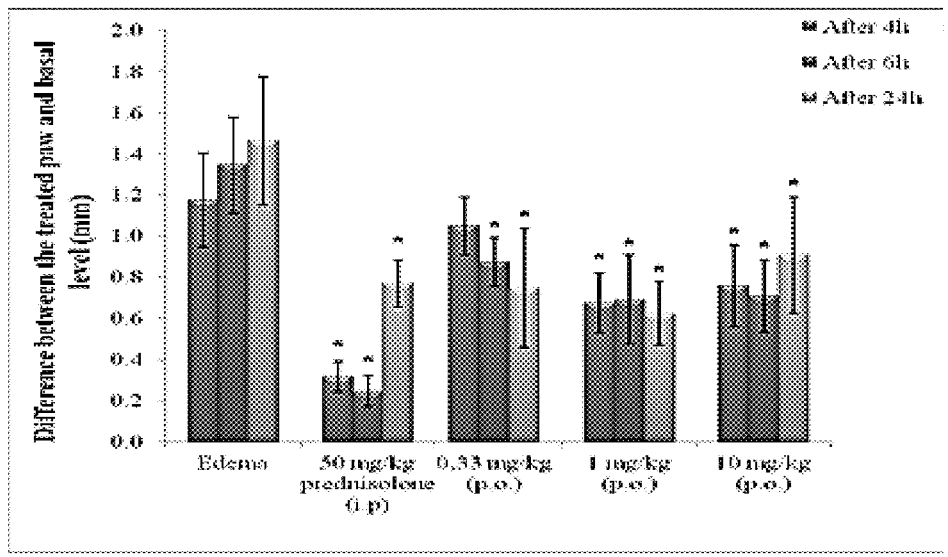
FIG. 3 shows the difference between treated and untreated paw edema after 4, 6 and 24 hours. "Preparation 1" reduces paw edema rate (in comparison to the control group) by 43.2%-57.5%. Data presented as group averages ± SN. Differences between control/edema and phytocannabinoid preparation groups are considered significant at $p<0.05*$.

Paw edema was reduced by all analysed doses of "Preparation 1". The most effective inhibition was observed at 1 mg/kg phytocannabinoid dose, which reduced the rates of paw edema (in comparison to the control group) by 43.2%-57.5% depicted in FIG. 3.

Figure 4:
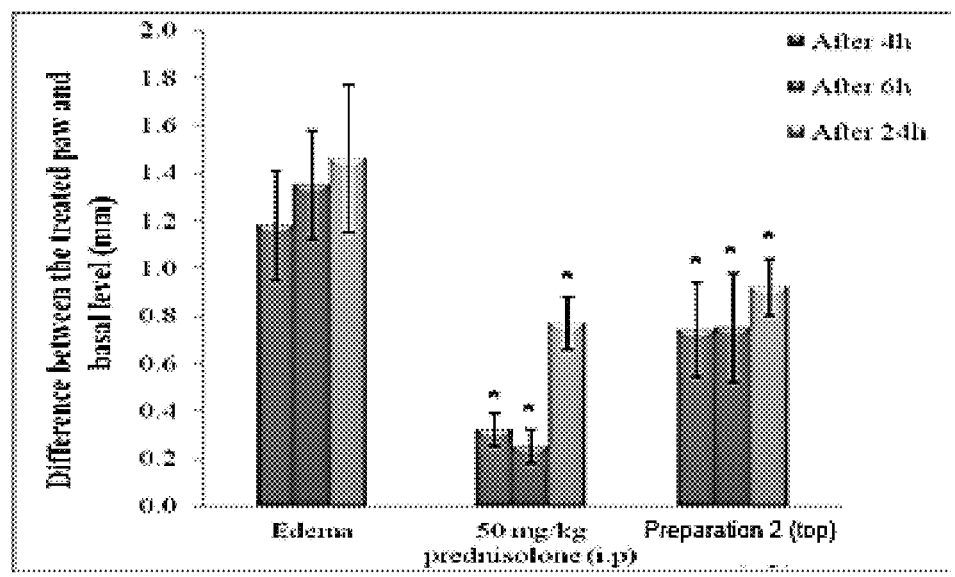
FIG. 4 shows the difference between treated and untreated paw edema after 4, 6 and 24 hours. "Preparation 2" statistically significantly reduced paw edema (up to 44.4%). Data presented as group averages ± SN. Differences between control/edema and phytocannabinoid preparation groups are considered significant at $p<0.05*$.

Local application of preparation "Preparation 2" statistically significantly reduced paw edema (up to 44.4%) as shown in FIG. 4.

CITED LITERATURE

1. Samuelsson, B. 1990. Arachidonic acid metabolism: Role in inflammation. *Zeitschrift Fur Rheumatologie* 50:3-6.
2. Fogh, Karsten, Troels Herlin, and Knud Kragballe. 1989. Eicosanoids in skin of patients with atopic dermatitis: Prostaglandin E 2 and leukotriene B 4 are present in biologically active concentrations. *Journal of Allergy and Clinical Immunology* 83 (2): 450-455.
3. Thomsen, Simon Francis. 2014. Atopic dermatitis: Natural history, diagnosis, and treatment. *ISRN Allergy* 2014: 354250.
4. Vasilopoulos, Y, M J Cork, R Murphy, H C Williams, D A Robinson, G W Duff, S J Ward, and R Tazi-Ahnini. 2004. Genetic association between an AACC insertion in the 3'UTR of the stratum corneum chymotryptic enzyme gene and atopic dermatitis. *J Invest Dermatol* 123 (1): 62-6.
5. Hovnanian, Alain. 2013. Netherton syndrome: Skin inflammation and allergy by loss of protease inhibition. *Cell Tissue Res* 351 (2): 289-300.
6. van Smeden, Jeroen and Joke A Bouwstra. 2016. Stratum corneum lipids: Their role for the skin barrier function in healthy subjects and atopic dermatitis patients. *Curr Probl Dermatol* 49:8-26.
7. Grether-Beck, Susanne, Ingo Felsner, Heidi Brenden, Zippora Kohne, Marc Majora, Alessandra Marini, Thomas Jaenicke, et al. 2012. Urea uptake enhances barrier function and antimicrobial defense in humans by regulating epidermal gene expression. *J Invest Dermatol* 132 (6): 1561-72.
8. Fluhr, J W, R Darlenski, and C Surber. 2008. Glycerol and the skin: Holistic approach to its origin and functions. *Br J Dermatol* 159 (1): 23-34.
9. Imokawa, G, A Abe, K Jin, Y Higaki, M Kawashima, and A Hidano. 1991. Decreased level of ceramides in stratum corneum of atopic dermatitis: An etiologic factor in atopic dry skin? *J Invest Dermatol* 96 (4): 523-6.
10. Chiba, Hideki, Makoto Osanai, Masaki Murata, Takashi Kojima, and Norimasa Sawada. 2008. Transmembrane proteins of tight junctions. *Biochimica Et Biophysica Acta (BBA)—Biomembranes* 1778 (3): 588-600.
11. Brandt, Eric B and Umasundari Sivaprasad. 2011. Th2 cytokines and atopic dermatitis. *Journal of Clinical & Cellular Immunology* 2 (3).
12. Biedermann, Tilo, Yuliya Skabytska, Susanne Kaesler, and Thomas Volz. 2015. Regulation of T cell immunity in atopic dermatitis by microbes: The yin and yang of cutaneous inflammation. *Front Immunol* 6:353.
13. Benenson, Shmuel, Oren Zimhony, David Dahan, Michal Solomon, David Raveh, Yechiel Schlesinger, and A M Yinnon. 2005. Atopic dermatitis—a risk factor for invasive *Staphylococcus aureus* infections: Two cases and review. *Am J Med* 118 (9): 1048-51.
14. Moody, M N, L K Morrison, and S K Tyring. 2010. Retapamulin: What is the role of this topical antimicrobial in the treatment of bacterial infections in atopic dermatitis? *Skin Therapy Lett* 15 (1): 1-4.
15. Blanter, Maximilian, Jennifer Vickers, Marian Russo, and Bijan Safai. 2015. Eczema herpeticum: Would you know it if you saw it? *Pediatr Emerg Care* 31 (8): 586-8.
16. Searing, Daniel A and Donald Y M Leung. 2010. Vitamin D in atopic dermatitis, asthma and allergic diseases. *Immunol Allergy Clin North Am* 30 (3): 397-409.
17. Omata, N, H Tsukahara, S Ito, Y Ohshima, M Yasutomi, A Yamada, M Jiang, et al. 2001. Increased oxidative stress in childhood atopic dermatitis. *Life Sci* 69 (2): 223-8.
18. Kim, Jung Eun, Hyun Jeong Kim, Bark-Lynn Lew, Kyung Ho Lee, Seung Phil Hong, Yong Hyun Jang, Kui Young Park, et al. 2015. Consensus guidelines for the treatment of atopic dermatitis in korea (part II): Systemic treatment. *Ann Dermatol* 27 (5): 578-92.
19. Del Rosso, James Q and Jacqueline Levin. 2011. The clinical relevance of maintaining the functional integrity of the stratum corneum in both healthy and disease-affected skin. *J Clin Aesthet Dermatol* 4 (9): 22-42.

20. Trouba, Kevin J, Hisham K Hamadeh, Rupesh P Amin, and Dori R Germolec. 2002. Oxidative stress and its role in skin disease. *Antioxidants and Redox Signaling* 4 (4): 665-673.
21. Okayama, Yoshimichi. 2005. Oxidative stress in allergic and inflammatory skin diseases. *Current Drug Targets—Inflammation & Allergy* 4 (4): 517-519.
22. McQuestion, Maurene. 2006. Evidence-based skin care management in radiation therapy. In *Seminars in Oncology Nursing*.
23. Hill, Alicia, Miriam Hanson, Melissa A Bogle, and Madeleine Duvic. 2004. Severe radiation dermatitis is related to *Staphylococcus aureus*. *Am J Clin Oncol* 27 (4): 361-3.
24. Smith, Margaret Mary and Melrose, James. 2015. Proteoglycans in Normal and Healing Skin. *Adv Wound Care (New Rochelle)* 4(3): 152-173.
25. Ghatak, Shibnath et al. 2015. Roles of Proteoglycans and Glycosaminoglycans in Wound Healing and Fibrosis. *International Journal of Cell Biology*. Review.
26. Fisar, Zdenek. 2009. Phytocannabinoids and endocannabinoids. *Current Drug Abuse Reviews* 2 (1): 51-75.
27. Pertwee, R G. 2008. The diverse CB1 and CB2 receptor pharmacology of three plant cannabinoids: Delta9-tetrahydrocannabinol, cannabidiol and delta9-tetrahydrocannabivarin. *Br J Pharmacol* 153 (2): 199-215.
28. Hassan, Samia, Khalil Eldeeb, Paul J Millns, Andrew J Bennett, Stephen P H Alexander, and David A Kendall. 2014. Cannabidiol enhances microglial phagocytosis via transient receptor potential (TRP) channel activation. *Br J Pharmacol* 171 (9): 2426-39.
29. Izzo, Angelo A, Francesca Borrelli, Raffaele Capasso, Vincenzo Di Marzo, and Raphael Mechoulam. 2009. Non-psychotropic plant cannabinoids: New therapeutic opportunities from an ancient herb. *Trends Pharmacol Sci* 30 (10): 515-27.
30. Ryan, Duncan, Alison J Drysdale, Carlos Lafourcade, Roger G Pertwee, and Bettina Platt. 2009. Cannabidiol targets mitochondria to regulate intracellular ca2+ levels. *J Neurosci* 29 (7): 2053-63.
31. Takeda, Shuso, Koichiro Misawa, Ikuo Yamamoto, and Kazuhito Watanabe. 2008. Cannabidiolic acid as a selective cyclooxygenase-2 inhibitory component in *cannabis*. *Drug Metab Dispos* 36 (9): 1917-21.
32. van der Stelt, Mario and Vincenzo Di Marzo. 2005. Anandamide as an intracellular messenger regulating ion channel activity. *Prostaglandins Other Lipid Mediat* 77 (1-4): 111-22.
33. Ramer, Robert, Katharina Heinemann, Jutta Merkord, Helga Rohde, Achim Salamon, Michael Linnebacher, and Burkhard Hinz. 2013. COX-2 and ppar-γ confer cannabidiol-induced apoptosis of human lung cancer cells. *Mol Cancer Ther* 12 (1): 69-82.
34. Hampson, A J, M Grimaldi, J Axelrod, and D Wink. 1998. Cannabidiol and (−)delta9-tetrahydrocannabinol are neuroprotective antioxidants. *Proc Natl Acad Sci USA* 95 (14): 8268-73.
35. Schwitzer, Thomas, Raymund Schwan, Karine Angioi-Duprez, Isabelle Ingster-Moati, Laurence Lalanne, Anne Giersch, and Vincent Laprevote. 2015. The cannabinoid system and visual processing: A review on experimental findings and clinical presumptions. *Eur Neuropsychopharmacol* 25 (1): 100-12.
36. Maccarrone, M and A Finazzi-Agro. 2003. The endocannabinoid system, anandamide and the regulation of mammalian cell apoptosis. *Cell Death & Differentiation* 10 (9): 946-955.
37. Wilkinson, Jonathan D and Elizabeth M Williamson. 2007. Cannabinoids inhibit human keratinocyte proliferation through a non-cb1/CB2 mechanism and have a potential therapeutic value in the treatment of psoriasis. *J Dermatol Sci* 45 (2): 87-92.
38. Nagarkatti, Prakash, Rupal Pandey, Sadiye Amcaoglu Rieder, Venkatesh L Hegde, and Mitzi Nagarkatti. 2009. Cannabinoids as novel anti-inflammatory drugs. *Future Medicinal Chemistry* 1 (7): 1333-1349.
39. Pommier, P, F Gomez, M P Sunyach, A D'Hombres, C Carrie, and X Montbarbon. 2004. Phase III randomized trial of *Calendula officinalis* compared with trolamine for the prevention of acute dermatitis during irradiation for breast cancer. *J Clin Oncol* 22 (8): 1447-53.
40. Babaee, Neda, Dariush Moslemi, Mohammad Khalilpour, Fatemeh Vejdani, Yasaman Moghadamnia, Ali Bijani, Mahmoud Baradaran, et al. 2013. Antioxidant capacity of *Calendula officinalis* flowers extract and prevention of radiation induced oropharyngeal mucositis in patients with head and neck cancers: A randomized controlled clinical study. *Daru* 21 (1): 18.
41. Patent EP2444081B 1
42. U.S. Pat. No. 6,949,582B1
43. Patent US20120264818A1

The invention claimed is:

1. A topical composition comprising: about 8.76% Caprylic/capric triglyceride, 5.64% *Aloe barbadensis* leaf juice, 0.94% Stearic acid, 0.52% Glycerol monostearate, 0.25% Trietanolamine, 0.4% Vitamin E, 3.33% Olive *europaea* Fruit Oil, 3.33% Glycerol, 0.6% Acrylates/C10-30 alkyl acrylate crosspolymer, 0.07% *Calendula Officinalis* Flower Extract, 0.8% Phenoxyethanol, and water,
   wherein the composition further comprises 0.75-1% of a *Cannabis sativa* extract in decarboxylated form and containing 0.25% of CBD, and 0.75-1% of the *Cannabis sativa* extract in non-carboxylated form and containing 0.25% CBDA, wherein the *Cannabis sativa* extract comprises about 80% of CBDA from the total cannabinoids, and THC is less than 0.1%.

2. A topical composition according to claim 1, wherein the *Cannabis sativa* extract is made from any non-psychotropic *Cannabis sativa* variety.

3. The topical composition according to claim 2, wherein the *Cannabis sativa* extract is made from the Benico variety.

4. A topical composition according to claim 1 with a dynamic viscosity from 2100 to 2300 mPa and a pH of about 6.

* * * * *